United States Patent
Pilgaonkar et al.

(10) Patent No.: US 10,806,685 B2
(45) Date of Patent: Oct. 20, 2020

(54) ORAL CARE COMPOSITIONS

(71) Applicant: RUBICON RESEARCH PRIVATE LIMITED, Mumbai (IN)

(72) Inventors: Pratibha Sudhir Pilgaonkar, Mumbai (IN); Maharukh Tehmasp Rustomjee, Mumbai (IN); Anilkumar Surendrakumar Gandhi, Mumbai (IN)

(73) Assignee: RUBICON RESEARCH PRIVATE LIMITED, Thane (W) (IN)

( * ) Notice: Subject to any disclaimer, the term of this patent is extended or adjusted under 35 U.S.C. 154(b) by 0 days.

(21) Appl. No.: 14/347,133

(22) PCT Filed: Sep. 28, 2012

(86) PCT No.: PCT/IN2012/000651
§ 371 (c)(1),
(2) Date: Mar. 25, 2014

(87) PCT Pub. No.: WO2013/072932
PCT Pub. Date: May 23, 2013

(65) Prior Publication Data
US 2014/0227202 A1   Aug. 14, 2014

(30) Foreign Application Priority Data

Sep. 30, 2011   (IN) .......................... 2795/MUM/2011

(51) Int. Cl.
| | | |
|---|---|---|
| *A61K 8/365* | (2006.01) | |
| *A61K 8/25* | (2006.01) | |
| *A61K 8/36* | (2006.01) | |
| *A61Q 11/00* | (2006.01) | |
| *A61K 33/06* | (2006.01) | |
| *A61K 8/02* | (2006.01) | |
| *A61K 8/19* | (2006.01) | |
| *A61K 8/34* | (2006.01) | |

(52) U.S. Cl.
CPC ............ *A61K 8/365* (2013.01); *A61K 8/0216* (2013.01); *A61K 8/19* (2013.01); *A61K 8/25* (2013.01); *A61K 8/345* (2013.01); *A61K 8/36* (2013.01); *A61Q 11/00* (2013.01)

(58) Field of Classification Search
CPC ...... A61K 8/345; A61K 8/0216; A61K 8/365; A61K 8/19; A61K 8/25; A61K 8/36; A61Q 11/00
See application file for complete search history.

(56) References Cited

U.S. PATENT DOCUMENTS

2009/0087485 A1*   4/2009   Pilgaonkar ........... A61K 9/0056
424/464

FOREIGN PATENT DOCUMENTS

| CN | 1861039 A | 11/2006 |
|---|---|---|
| WO | WO-2004047663 A2 | 6/2004 |

OTHER PUBLICATIONS

Avantor "Performance Materials", https://www.avantormaterials.com/Pharmaceutical/Products/Pharmaceutical-Excipients/PanExcea-Multi-Functional-and-Co-Processed-Performance-Excipients.aspx, pp. 1-2, Apr. 10, 2011.*
International Search Report issued in PCT/IN2012/000651 dated Jun. 20, 2013.

* cited by examiner

Primary Examiner — Lezah Roberts
(74) Attorney, Agent, or Firm — Blank Rome LLP

(57) ABSTRACT

The present invention relates to oral care compositions and to method of maintaining oral health. The oral care composition of the present invention comprises at least one carbon dioxide source, at least one acid source, at least one abrasive and one or more pharmaceutically acceptable excipients.

9 Claims, No Drawings

ORAL CARE COMPOSITIONS

This application is a U.S. national phase of International Patent Application No. PCT/IN2012/000651, filed Sep. 28, 2012, which claims the benefit of Indian Patent Application No. 2795/MUM/2011, filed Sep. 30, 2011.

FIELD OF THE INVENTION

The present invention relates to oral care compositions and to method of maintaining oral health. Particularly the oral care composition of the present invention comprises at least one carbon dioxide source, at least one acid source, at least one abrasive and one or more pharmaceutically acceptable excipients.

BACKGROUND OF THE INVENTION

Oral hygiene is the most vital part of dental care and is necessary for the prevention of dental caries, periodontal diseases, bad breath and other dental problems. Children and young adults are most susceptible to caries while adults are more prone to periodontal diseases which are the leading cause of tooth loss. Plaque build-up is recognized as the principal contributor to such diseases. Halitosis (oral malodor or bad breath) is also another oral problem that is typically attributed to bacterial activity in the mouth.

Maintenance of oral hygiene involves keeping the mouth, teeth, and gums clean and healthy by removing plaque and bacteria to prevent dental problems. A variety of oral products or dentifrices such as toothpastes, mouth rinses, tooth powder, and the like have been used over years for the maintenance of oral health. For ideal oral hygiene, the teeth should be brushed or rinsed with a dentifrice, flossed and irrigated following each meal and snack. But unfortunately, the time restraints in the lives of most people and the lack of convenient facilities do not allow this luxury. It is thus desirable to have means for cleaning and removing plaque from the teeth to protect mouth from gum diseases and bad breath, which is not only convenient and easy to use but also provides optimum cleaning and plaque reducing and anti-caries properties.

U.S. Pat. No. 5,804,165 discloses a non-liquid oral dentifrice composition in the form of powder or tablets which is characterized by an efficacious ratio of carbon dioxide source, xylitol, acid source and silica. Anhydrous, solid, effervescent compositions and having plaque reducing properties have been discussed. U.S. Pat. No. 5,817,294 discloses an effervescent tablet or capsule of effervescent powder for oral use comprising a non-aqueous, water soluble carbon dioxide source; non-aqueous, water soluble acid source; and non-aqueous limited aqueous solubility plaque adsorbent such as natural and synthetic silicas.

Various dentifrice compositions developed by researchers commonly contain a silica abrasive for controlled mechanical cleaning, plaque removal and polishing of teeth. Most conventional silicas used in dentifrices have negatively charged surfaces that tend to interact with other co-ingredients of the dentifrice, leading to undesirable compatibility issues. Amongst other agents that can interact with silica most representative include fluorides and zinc compounds, flavorants, perfumes and the like. Silicas are also not adequately compatible with tin, strontium and the like. Presence of such incompatibilities of silica in any dentifrice product results in unavailability of the other ingredients to elicit their beneficial applications. Also small particle size of silica results in blends with very poor flow properties causing weight and content variation in the final dosage forms. Further the intended use of an abrasive substance in oral care is to remove various organic deposits as well as plaque from the surface of the teeth without causing undue abrasion to the tooth tissues.

Accordingly need exists to develop dentifrice or oral care compositions which not only comprise compatible additives but also comprise abrasives that are effective at removing undesirable deposits with optimum abrasion. The present inventors after thorough research address this need and provide a complete oral care product that overcomes drawbacks associated with the use of conventional abrasives like silica.

The present invention provides an oral care composition that cleans the oral cavity of organic debris and removes plaque from the teeth thereby promoting healthy tooth maintenance and providing fresh breath. Such an oral care product has inherent stability and improved shelf life. Furthermore the compositions of the present invention are presented in convenient; easy to use fast dissolving dosage forms that can be used anytime anywhere with or without water or toothbrush. The compositions of the present invention can provide complete oral care by not only maintaining oral hygiene, but also by providing preventive or therapeutic oral benefits and serving as an aid during any dental procedures.

SUMMARY OF THE INVENTION

The present invention relates to oral care compositions comprising at least one carbon dioxide source, at least one acid source, at least one abrasive and one or more pharmaceutically acceptable excipients.

DETAILED DESCRIPTION OF THE INVENTION

The present invention relates to oral care compositions and to method of maintaining oral health. Particularly the composition of the present invention comprises at least one carbon dioxide source, at least one acid source, at least one abrasive and one or more pharmaceutically acceptable excipients.

The term "oral care composition" as used herein refers to any composition suitable for administration to the oral cavity of a human or animal subject for maintaining and/or improving the oral health and hygiene of the subject, and/or for preventing or treating a condition or disorder of the teeth, gums, mucosa or other hard or soft tissues of the oral cavity and/or for providing beneficial action during any dental procedures.

Carbon dioxide source present in the composition of the present invention includes, but is not limited to, bicarbonate salt, carbonate salt or mixtures thereof. A pharmaceutically acceptable bicarbonate or carbonate salt includes, but is not limited to, bicarbonate salt of an alkali or an alkaline earth metal; carbonate salt of alkali or alkaline earth metal; and the like or mixtures thereof. In one embodiment, a pharmaceutically acceptable bicarbonate or carbonate salt includes, but is not limited to, sodium bicarbonate, sodium carbonate, potassium bicarbonate, potassium carbonate, lithium bicarbonate, lithium carbonate, calcium carbonate, magnesium carbonate, ammonium carbonate, ammonium bicarbonate, lithium hydrogen carbonate, sodium sesquicarbonate, sodium glycine carbonate, aluminum bicarbonate and the like or combinations thereof. In one embodiment the compositions of the present invention comprise about 5% to about 90% by weight of the carbon dioxide source. In another embodiment the compositions of the present invention comprise about 10% to about 75% by weight of the carbon dioxide source.

Acid source present in the compositions of the present invention includes, but is not limited to, pharmaceutically acceptable organic acid, inorganic acid, salt or partial salt of an organic acid or inorganic acid or any mixtures thereof. Non-limiting examples of such organic acids are citric acid, adipic acid, ascorbic acid, malic acid, tartaric acid, succinic acid, pyruvic acid, oxaloacetic acid, maleic acid, alpha-ketoglutaric, fumaric acid, isocitric acid, alginic acid, amino acids, cis-aconitic acid, lactic acid, and the like or combinations thereof. Suitable inorganic acids include, but are not limited to, phosphoric acid. Salts or partial salts of such organic or inorganic acids that may be employed in the present invention include, but are not limited to, alkali or alkaline earth metal salts of maleic acid, citric acid, adipic acid, malic acid, ascorbic acid, succinic acid, fumaric acid, and the like or combinations thereof. In one embodiment, salts or partial salts of such organic or inorganic acids that may be employed in the present invention include, but are not limited to, calcium, lithium, sodium, potassium and magnesium salts of maleic acid, citric acid, adipic acid, malic acid, ascorbic acid, succinic acid, fumaric acid, phosphoric acid and the like or combinations thereof. In one embodiment the acid source employed in the composition of the present invention is citric acid and/or tartaric acid. In one embodiment the compositions of the present invention comprise about 1% to about 50% by weight of the acid source. In another embodiment the compositions of the present invention comprise about 3% to about 30% by weight of the acid source.

In one embodiment, carbon dioxide source is used in the compositions of the present invention in an amount such that the acid source is completely neutralized by it. In another embodiment, carbon dioxide source is used in the compositions of the present invention in an amount such that the acid source is completely neutralized by it and a further excess of the carbon dioxide source is employed such that a basic pH of the saliva solution is maintained from about 1 minute to about 1 hour or more.

The compositions of the present invention comprising at least one carbon dioxide source, at least one acid source, further comprises at least one abrasive. Abrasive employed in the composition of the present invention includes, but is not limited to, dicalcium phosphate dihydrate, dicalcium phosphate monohydrate, anhydrous dicalcium phosphate, tricalcium phosphate, calcium pyrophosphate, sodium metaphosphate, aluminum hydroxide, zirconium silicate, calcium carbonate, calcium hydrogen phosphates, zeolites, hydroxyapatite, alumina, aluminosilicate, calcium silicate, calcium aluminate, magnesium carbonate, magnesium phosphate, sodium metaphosphate, bentonite, talc, sodium aluminum silicate, melamines, phenolics, ureas, melamine-ureas, melamine-formaldehydes, urea-formaldehydes, melamine-urea-formaldehydes, cross-linked epoxides, cross-linked polyesters, alumina-based ceramics, zirconia, titanium diboride, pumice, co-processed abrasive and the like or combinations thereof.

In one embodiment, the abrasive that may be employed in the composition of the present invention is a silicate. Suitable silicates that may be employed in the composition of the present invention include, but are not limited to, zirconium silicate, aluminosilicate, calcium silicate, magnesium silicate, aluminum silicate, and the like or combinations thereof. In another embodiment, the abrasive that may be employed in the composition of the present invention is calcium silicate. The abrasives employed in the compositions of the present invention provide optimum abrasive power and debris and plaque removal properties.

In a further embodiment, the abrasive employed in the composition of the present invention is a co-processed abrasive. In another embodiment, the co-processed abrasive that may be employed includes, but is not limited to, co-processed calcium silicate, co-processed magnesium silicate and the like or a combination thereof. In one embodiment, co-processed abrasive employed in the composition of the present invention is co-processed magnesium silicate, such as, but not limited to, magnesium silicate co-processed with starch, magnesium silicate co-processed with chitin, and the like, or combinations thereof. In another embodiment, co-processed abrasive employed in the composition of the present invention is co-processed calcium silicate. In a further embodiment, co-processed calcium silicate that may be employed includes, but is not limited to, calcium silicate co-processed with cross-linked polyvinyl pyrrolidone, calcium silicate co-processed with water-soluble excipient, calcium silicate co-processed with chitin, and the like or combinations thereof. In one embodiment, co-processed calcium silicate employed may be calcium silicate co-processed with water-soluble excipient. In another embodiment, water soluble excipient such as, but not limited to, a carbohydrate, a water soluble salt or a polyhydric alcohol or its derivative, and the like or combinations thereof may be employed. In a further embodiment, calcium silicate co-processed with water soluble carbohydrate is employed in the oral care compositions of the present invention. Further the use of, co-processed abrasive provides optimum abrasive power to the dentifrice composition for plaque and debris removal without causing any harsh effect or undue abrasion on the tooth surface or tooth enamel or dentine.

The water soluble carbohydrate employed in the co-processed calcium silicate may be, but is not limited to monosaccharide, disaccharide, oligosaccharide or polysaccharide. Non-limiting examples of monosaccharides employed are xylose, glucose, mannose, fructose, and galactose. Non-limiting examples of disaccharide employed are maltose, lactose, cellobiose, sucrose, mannitol and trehalose. Non-limiting examples of oligosaccharide are raffinose and dextrates. Non-limiting examples of polysaccharides are maltodextrins. The water soluble salt that may be employed in the co-processed calcium silicate includes, but is not limited to, sodium chloride, and the like. The water soluble polyhydric alcohol that may be employed in the co-processed calcium silicate includes, but is not limited to, propylene glycol, polyethylene glycol and glycerin, and the like or combination thereof. The water soluble excipient and calcium silicate can be present in the co-processed excipient in a ratio of water-soluble excipient to water insoluble excipient of from about 50:1 to about 1:50. PCT Publication WO2007/113856A2 that has been incorporated herein as a reference describes co-processed calcium, silicate excipient. The term "co-processed" as used herein refers to a composite excipient in which at least two excipients are present in close proximity to each other. In one embodiment, co-processed excipient is a composite excipient in which at least two excipients are present in close proximity to each other, with one excipient being incorporated in the particle structure of the other.

In one embodiment, the co-processed abrasive employed in the composition of the present invention is calcium silicate co-processed with mannitol. In a further embodiment, the co-processed calcium silicate employed in the composition of the present invention is calcium silicate co-processed with mannitol. In another embodiment, the co-processed calcium silicate and mannitol employed in the compositions of the present invention is PanExcea™.MC 200G available from Avantor™, US. Without being bound to any theory, it is believed that the use of co-processed calcium silicate and mannitol overcomes the drawbacks otherwise associated with the use of silica or in certain cases with silicates as abrasive in dentifrice or oral care compositions, since in the co-processed form calcium silicate is substantially covered with mannitol which in turn substantially reduces the interaction of calcium silicate with any other excipients used in the composition or any other metallic surfaces during processing and production. Furthermore the use of co-processed calcium silicate and mannitol does not compromise on the abrasive or adsorbent properties of calcium silicate but in fact provides optimum abrasive and adsorbent properties to the oral composition along with good dispersibility and pleasant taste. The use of co-processed calcium silicate and mannitol thereby serves the purpose of helping in rapid dissolution of the dosage form while providing necessary adsorbent and abrasive properties. The use of co-processed calcium silicate does not present any flow issues and thereby does not present any content uniformity problems.

In one embodiment, the abrasive employed in the composition of the present invention may be a combination of a co-processed abrasive and a non co-processed abrasive listed under abrasives mentioned above.

In one embodiment, composition of the present invention comprises about 1% to about 95% by weight of abrasive. In one embodiment, composition of the present invention comprises about 5% to about 95% by weight of abrasive. In one embodiment, composition of the present invention comprises about 10% to about 95% by weight of abrasive. In another embodiment composition of the present invention comprises about 1% to about 95% by weight of calcium silicate. In another embodiment composition of the present invention comprises about 5% to about 95% by weight of calcium silicate. In another embodiment composition of the present invention comprises about 10% to about 95% by weight of calcium silicate. In one embodiment composition of the present invention comprises about 1% to about 95% by weight of co-processed abrasive. In one embodiment composition of the present invention comprises about 5% to about 95% by weight of co-processed abrasive. In one embodiment composition of the present invention comprises about 10% to about 95% by weight of co-processed abrasive. In one embodiment composition of the present invention comprises about 1% to about 95% by weight of co-processed calcium silicate. In one embodiment composition of the present invention comprises about 5% to about 95% by weight of co-processed calcium silicate. In one embodiment composition of the present invention comprises about 10% to about 95% by weight of co-processed calcium silicate.

One or more pharmaceutically acceptable excipients may be employed in the oral compositions of the present invention. These include, but are not limited to, sweetening agents, flavouring agents, surfactants, viscosity modifiers, binders, disintegrants, glidants, anti-adherents, lubricants, diluents, humectants, chelating or sequestering agents, pH modifiers, buffering agents, opacifiers, colorants or pigments, adhesives, liquid carriers and the like or mixtures thereof.

The sweeteners or sweetening agents employed in the compositions of the present invention include, but are not limited to, dextrose, xylitol, mannitol, sorbitol, fructose, maltose, maltodextrin, sodium saccharin, calcium cyclamate, aspartame (N-L-alpha-aspartyl-L-phenylalanine methyl ester), neohesperidin, acesulfame potassium, sucralose, dihydrochalcone, and the like or combinations thereof. In one embodiment, the sweetening agent employed includes, but is not limited to, natural sweetener, artificial sweetener or combinations thereof. In another embodiment the sweetener employed in the present invention is a non-caloric sweetener. In one embodiment, co-processed adsorbent employed in the composition of the present invention comprises calcium silicate and mannitol and thereby due to the presence of mannitol, the co-processed excipient also serves to make the composition palatable. The co-processed abrasive such as co-processed calcium silicate employed in the compositions of the present invention, thereby serves as a plaque or organic debris adsorbent, an abrasive, a dispersing agent or a sweetening agent. In one embodiment, the sweetening agent employed in the composition of the present invention is xylitol. Xylitol, in addition to its sweetening properties, enhances product stability by exhibiting specific bacteriostatic and bacteriocidal properties. It is also helpful in reducing dental caries by inhibiting growth of cariogenic *Streptococcus mutans* bacteria. It has equal sweetness intensity to sucrose, but unlike sucrose, xylitol is non-cariogenic. In addition, xylitol also has distinctive cooling effect desirable in oral products. In one embodiment the sweeteners are employed in the compositions of the present invention in an amount of about 1% to 75% by weight of the composition.

The oral care composition of the present invention is flavored with flavouring agents such as, but not limited to, non-aqueous liquid flavoring agents or solid flavoring agents or essential oils and the like or combinations thereof. Non-limiting examples of flavouring agents that may be employed include, but are not limited to, menthol, thymol, wintergreen oil, eucalyptus oil, fennel oil, tea tree oil, lemon oil, myrrh oil, methyl salicylate, peppermint oil, oil of cloves, extract of vanilla, cinnamon powder, spearmint flavoring, strawberry flavoring, mint flavoring, bubble gum flavoring, orange flavoring extract, lemon flavoring extract, cherry flavoring, chocolate flavoring, and the like or combinations thereof.

Furthermore a surfactant may be used in the compositions of the present invention to aid in the prophylactic action and in dispersion of the composition throughout the oral cavity. The surfactants that may be employed in the compositions of the present invention include, but are not limited to, anionic, nonionic, cationic or amphoteric type or combinations thereof. A pharmaceutically acceptable surfactant that may be used in the compositions of the present invention includes, but is not limited to, higher alkyl sulfates, such as, but not limited to, sodium lauryl sulfate and the like; water soluble salts of sulfonated monoglycerides of higher fatty acids, such as, but not limited to, sodium coconut monoglyceride sulfonate and the like; glycerol fatty acid esters; acetylated glycerol fatty acid esters; lower alcohol fatty acids esters; propylene glycol fatty acid esters; sorbitan fatty acid esters; polyethylene glycol (PEG) sorbitan fatty acid esters, such as, but not limited to, PEG-40 sorbitan diisostearate; salts of higher fatty acid amides or lower aliphatic amino acids, such as, but not limited to, taurine or sarcosine, sodium N-methyl-N-palmitoyl taurinate, sodium N-lauryl or sarcosinate, sodium N-myristyl sarcosinate, sodium N-palmitoyl sarcosinate and the like, or combinations thereof. Suitable surfactants may be used as emulsifying or suspending agents.

Optionally, the compositions of the present invention may comprise pharmaceutically acceptable viscosity modifiers that can modify the viscosity of the saliva mixture formed when the composition is administered in the oral cavity and inhibit the escape of carbon dioxide gas to maintain a high oral bicarbonate ion concentration. Non-limiting examples of the viscosity modifiers that may be employed include, but are not limited to, gums and thickening agents such as, but not limited to, carboxymethyl cellulose, gum tragacanth, gum arabic, gum Karaya, sodium alginate, hydroxyethyl cellulose, methyl and ethyl cellulose, carrageenan, xanthan gum, polyvinyl pyrrolidone, silica aerogels and the like, or combinations thereof.

The compositions of the present invention may further include at least one disintegrant or superdisintegrant such as, but not limited to, natural, modified or pregelatinized starch, crospovidone, croscarmellose sodium, sodium starch glycolate, low-substituted hydroxypropyl cellulose, and the like or combinations thereof. Suitable binders employed in the compositions of the present invention include, but are not limited to, starch, pregelatinized starch, polyvinyl pyrrolidone, copovidone, cellulose derivatives, such as, but not limited to, hydroxypropylmethyl cellulose, hydroxypropyl cellulose and carboxymethyl cellulose and their salts, and the like or any combinations thereof. Suitable diluents include, but are not limited to, starch, microcrystalline cellulose, lactose, maltose, fructose, guar gum, magnesium hydroxide, dicalcium phosphate, and the like or any combinations thereof. Suitable lubricants include, but are not limited to, magnesium stearate, calcium stearate, high molecular weight polyethylene glycol, stearic acid, talc, and sodium stearyl fumarate and the like, or mixtures thereof. The compositions of the present invention may also include a glidant such as, but not limited to, colloidal silicon dioxide, silica gel, precipitated silica, and the like or combinations thereof. The compositions of the present invention may also include an anti-adherent such as, but not limited to, colloidal silicon dioxide, silica gel, precipitated silica, and the like or combinations thereof. The compositions of the present invention may include humectants. Suitable humectants include, but are not limited to, polyethylene glycol (at a variety of different molecular weights), propylene glycol, glycerin (glycerol), hydrogenated starch hydrolyzates, and the like or mixtures thereof. Suitable chelating or sequestering agents such as but not limited to alkali metal salts of tartaric acid and citric acid, or alkali metal salts of pyrophosphates or polyphosphates may be included in the compositions.

Suitable buffering agents that may be employed include, but are not limited to, alkali metal hydroxides, carbonates, sesquicarbonates, borates, silicates, phosphates, imidazole, and mixtures thereof. Non-limiting examples of buffering agents that may be employed include, but are not limited to, monosodium phosphate, trisodium phosphate, sodium hydroxide, potassium hydroxide, alkali metal carbonate salts, sodium carbonate, imidazole, pyrophosphate salts, citric acid, and sodium citrate. Suitable pH modifiers that may be employed include, but are not limited to, citric acid, fumaric acid, malic acid and the like or combinations thereof. Suitable opacifiers, such as, but not limited to, titanium dioxide, cerium oxide ($CeO_2$), tin oxide ($SnO_2$), zirconium dioxide ($ZrO_2$) and the like may be employed. Suitable pigment or colorant may be included, such as, but are not limited to, a dye, an aluminum lake, caramel; colorant based upon iron oxide, and the like or mixture thereof.

Optionally adhesives such as but not limited to resins and other bioadhesives may be employed in the formulations. Optionally, the compositions of the present invention comprise pharmaceutically acceptable liquid carriers, such as, but not limited to; glycerol, polyethylene glycol, and the like or any mixtures thereof. Optionally, other abrasives may be incorporated in the present compositions such as silicon, silica, and the like or combinations thereof. In one embodiment, the composition of the present invention does not contain alcohol.

In one embodiment, in addition to one or more pharmaceutically acceptable excipient, the oral compositions of the present invention may further comprise oral care actives or agents. Suitable oral care actives or agents that may be incorporated include, but are not limited to, anti-bacterial, antimicrobial, anti-plaque agents, astringent agents, desensitizing agents, fluoride containing anticaries agents, hydrogen peroxide source, tartar control agents, anticalculus agents, fluoride ion sources, stannous ion sources, anesthetic agents, whitening agents, tooth strengthening agents, antimalodor agents, anti-gingivitis agents, anti-periodontitis agents, anti-sensitivity agents, anti-erosion agents, anti-xerostomia agents, occlusion agents, antiseptic agents, antioxidants, proteolytic enzymes, antistain agents, healing agents; nutrients, probiotics, remineralization agents, antiinflammatory agents, analgesic agents, antibiotics, vitamins, antiviral agents, antifungal agents and the like or combinations thereof.

Pharmaceutically acceptable antibacterial or antimicrobial or antiplaque agents may be incorporated in the oral compositions of the present invention. Such compounds include, but are not limited to, trichlosan, chlorhexidine, hexetidine, delmopinol, zinc citrate, benzoic acid, sodium benzoate, potassium benzoate boric acid, phenolic compounds such as, but not limited to, betanapthol, chlorothymol, thymol, anethole, eucalyptol, menthol, phenol, amylphenol, hexylphenol, heptylphenol, octylphenol, hexylresorcinol and the like or combinations thereof; laurylpyridinium chloride, myristylpyridinium chloride, cetylpyridinium fluoride, cetylpyridinium chloride, cetylpyridinium bromide, cationic surface active agents, such as, but not limited to, di-isobutylphenoxyethoxyethyl dimethyl benzyl ammonium chloride, benzyl dimethyl stearyl ammonium chloride, tertiary amines, plant extracts such as, but not limited to, grapefruit extract, apple extract and the like or combinations thereof; essential oils including, but not limited to, thymol, geraniol, carvacrol, citral, hinokitiol, eucalyptol, catechol (particularly 4-allyl catechol) and the like or mixtures thereof; antibiotics, methyl salicylate, hexetidine, sanguinarine; and the like or combinations thereof.

Pharmaceutically acceptable astringent agents that may be employed in the compositions of the present invention, include, but are not limited to, aluminum sulfate, and the like. Pharmaceutically acceptable desensitizing agents may be employed in the compositions of the present invention. Desensitizing agents that may be employed in the composition include, but are not limited to, strontium chloride, potassium nitrate, zinc chloride, monosodium citrate, sodium nitrate, acetanilide, phenacetin, acertophan, thiorphan, spiradoline, aspirin, codeine, thebaine, levorphenol, hydromorphone, oxymorphone, phenazocine, fentanyl, buprenorphine, butarphanol, nalbuphine, pentazocine, natural herbs and the like or combinations thereof; and the like or mixtures thereof.

Pharmaceutically acceptable fluoride containing anti-caries agents may be employed in the compositions of the present invention such as, but are not limited to, stannous fluoride, sodium fluoride, sodium monofluorophosphate, amine fluoride, and the like or combinations thereof. Anti-calculus or tartar control agents may be incorporated into compositions of the present invention. Inorganic phosphorous tartar control or anti-calculus agents may include, but are not limited to, water-soluble pyrophosphates such as, but not limited to, disodium pyrophosphate, dipotassium pyrophosphate, tetrapotassium pyrophosphates or tetrasodium pyrophosphates and the like or combinations thereof. Organic phosphorous compounds that may serve as tartar control or anti-calculus agents include, but are not limited to, zinc citrate, polyolefin sulfonates, polyvinyl phosphates, polyamino propane sulfonic acid, polyphosphonates such as, but not limited to, disodium ethane-1-hydroxy-1,1-diphosphonate (EHDP), methanediphosphonic acid, and 2-phosphonobutane-1,2,4-tricarboxylic acid, polyvinyl phosphonate, polyolefin phosphonate, and the like or combinations thereof.

Fluoride ion sources such as, but not limited to, sodium fluoride, stannous fluoride, potassium fluoride, potassium stannous fluoride, sodium hexafluorostannate, stannous chlorofluoride, sodium fluorozirconate, sodium monofluorophosphate, zinc fluoride, zinc ammonium fluoride, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, sodium monofluorophosphate and the like or combinations thereof may be employed in the compositions of the present invention.

Suitable stannous ion sources such as, but not limited to, stannous fluoride, stannous chloride, stannous gluconate and the like or combinations thereof may be incorporated in the compositions of the present invention.

Whitening agents may be employed in the compositions of the present invention such as, but not limited to, peroxides, metal chlorites, perborates, percarbonates, peroxyacids, persulfates, and the like or combinations thereof. Suitable peroxide compounds include, but are not limited to, hydrogen peroxide, urea peroxide, calcium peroxide, carbamide peroxide, and the like or mixtures thereof. Pharmaceutically acceptable hydrogen peroxide source that may be employed in the compositions of the present invention, include, but are not limited to, sodium perborate, potassium perborate, disodium or dipotassium peroxy dicarbonate, sodium or potassium carbonate sequi (peroxy hydrate) and the like or combinations thereof. These compounds when wetted with water or saliva form hydrogen peroxide which is bactericide and whitening agent. Suitable metal chlorites include, but are not limited to, calcium chlorite, barium chlorite, magnesium chlorite, lithium chlorite, sodium chlorite, potassium chlorite and the like or combinations thereof. Additional bleaching substances may be employed such as, but not limited to, hypochlorite and chlorine dioxide.

Suitable tooth strengthening agents such as, but not limited to, bentonite may be employed in the compositions of the present invention. Suitable anti-malodor agents such as, but not limited to, higher alcohols selected from, but not limited to, 1-nonanol, 1-decanol and 1-undecanol, or mixtures thereof may be employed in the compositions of the present invention. Suitable antigingivitis agents such as, but not limited to, essential oils, tranexamic acid and the like or combinations thereof may be employed in the compositions of the present invention. Suitable remineralization agents include, but are not limited to, casein phosphopeptide-amorphous calcium phosphate, tricalcium phosphate, dicalcium phosphate dihydrate, and the like or combinations thereof.

Suitable anti-periodontitis agents such as, but not limited to, isothiocyanate compounds selected from the group consisting of ω-alkenyl isothiocyanate compounds, ω-alkylthioalkyl isothiocyanate compounds and the like or combinations thereof may be employed in the compositions of the present invention. Anesthetic agents such as, but not limited to, lidocaine, benzocaine and the like may incorporated in the compositions of the present invention.

Suitable anti-erosion agents such as, but not limited to, zinc oxide, phosphorylated polymers; polyphosphonates; polycarboxylates and carboxy-substituted polymers; copolymers of phosphate- or phosphonate-containing monomers or polymers with ethylenically unsaturated monomers, amino acids, or with other polymers selected from proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) or poly(vinyl benzyl chloride); metal ions selected from stannous, zinc and copper; and the like or mixtures thereof. Suitable anti-xerostomia agents such as, but not limited, to, glycerol triester compounds, xylitol containing oral products, carboxymethyl cellulose saliva substitute and the like or combinations thereof may be employed in the compositions of the present invention. Suitable occlusion agents, such as, but not limited to, arginine, calcium carbonate and the like or combinations thereof may be incorporated in the compositions of the present invention. Suitable antioxidants that may be included in the present invention include, but are not limited to vitamin E, ascorbic acid, uric acid, citric acid or salts, carotenoids, vitamin A, flavonoids and polyphenols, herbal antioxidants, melatonin, aminoindoles, lipoic acids and the like or mixtures thereof. Suitable, proteolytic enzymes useful for the compositions of the present invention include, but are not limited to papain, bromelain, chymotrypsin, ficin, alcalase and the like or combinations thereof. Non-limiting examples of nutrients include vitamins, minerals, amino acids and the like or combinations thereof.

Non-limiting examples of anti-inflammatory agents include non-steroidal anti-inflammatory agents (NSAIDS), oxicams, salicylates, propionic acids, acetic acids and fenamates and the like or combinations thereof. Suitable NSAIDS include, but are not limited to, ketorolac, flurbiprofen, ibuprofen, naproxen, diclofenac, etodolac, indomethacin, sulindac; tolmetin, ketoprofen, fenoprofen, piroxicam, nabumetone, aspirin, diflunisal, meclofenamate, mefenamic acid, oxyphenbutazone, phenylbutazone, acetaminophen and the like or combinations thereof. Non-limiting examples of analgesics include phenyloin, alfentanil, alphaprodine, buprenorphine, butorphanol, dihydromorphine, ethymethylthiambutene, fentanyl, hydrocodone, levorphanol, lofentanil, meperidine, pentazocine, sufentanil, and the like or combinations thereof. Non limiting examples of antiseptic agents include, but are not limited to, chlorhexidine gluconate, benzalkonium chloride, cetyl trimethylammonium bromide, cetylpyridinium chloride, benzethonium chloride, alcohol, sodium benzoate, sodium chloride, sodium bicarbonate and the like or combinations thereof.

Depending upon the oral care active included, the composition of the present invention can be employed for preventing and/or treating a condition or disorder of the teeth, gums, mucosa or other hard or soft tissues of the oral cavity and/or for providing beneficial action during any dental procedures.

The compositions of the present invention can be in the form of, but not limited to, fast dissolving powder, quick dissolving granules, fast dissolving tablet, bite dispersion tablets, capsules, films, lozenge, non-aqueous liquid mixtures, oral rinse, a mouth wash, toothpaste, tooth powder, oral tablet, denture product, chewing gum and the like. In one embodiment the composition of the present invention is used as an oral rinse, or a mouth wash. In one embodiment the composition of the present invention is in the form of effervescent dosage form. In one embodiment, the dosage form of the present invention is a non-aqueous dosage form. In one embodiment, the dosage form of the present invention can be used without water or toothbrush anytime anywhere for maintenance of oral hygiene. In another embodiment, the composition of the present invention is not completely soluble in saliva.

Without being bound to any theory, it is believed that when the composition of the present invention is placed in the oral cavity the saliva wets the composition dissolving some carbon dioxide source and acid source, generating effervescence. The resulting effervescent action sweeps the saliva mixture through the oral cavity, between the teeth, and the acid-base reaction product has a solubilizing effect on plaque components that loosens the plaque and other organic debris from the surface of the teeth. In an embodiment, when the abrasive employed in the composition of the present invention is co-processed abrasive, such as but not limited to, co-processed calcium silicate, the water soluble component of the co-processed calcium silicate adsorbent dissolves in the oral cavity, the released calcium silicate particles adsorb the swept away plaque or organic debris particles and also provide abrasive action on tooth surface, thereby effectively cleaning the teeth. Further the excess soluble acid in the saliva stimulates the salivary glands to secrete additional saliva. Generation of additional saliva further results in dissolution of the carbonate source and further cleaning action as discussed above till the dissolved carbon dioxide source is fully exhausted. The saliva solution can be swished through the mouth to clean surfaces of the teeth, to sweep out loosened organic debris and plaque particles. The saliva solution is allowed to remain in the oral cavity for some time of about 1 minute to enhance cleaning, action. The resulting saliva solution is then swallowed or expectorated. The adsorbent particles remaining after expectoration significantly safeguard the teeth, and gums from bacterial colonization till they eventually get flushed away by adsorbing plaque particles and organic debris, thereby reducing the level of plaque and mouth odor. The bicarbonate or carbonate ions of the carbon dioxide source are also adsorbed on the calcium silicate adsorbent and released after their levels in the saliva mixture is reduced, thereby providing prolonged beneficial action. In one embodiment, thus the dosage form of the present invention, upon insertion in the oral cavity liquefies in the mouth. In a further embodiment, the composition of the present invention when taken in the mouth, liquefies, generating effervescence and additional saliva and this saliva solution is swished through the mouth to clean the teeth and loosen organic debris and biomass; and finally either swallowed or expectorated. In one embodiment, the compositions of the present invention provide plaque adsorbing and cleansing action over a prolonged period of time. In another embodiment, the compositions of the present invention provide plaque adsorbing and cleansing action over a prolonged period of time even after the use of oral product.

The compositions of the present invention cleans tooth surface, effectively removes plaque, reduces tooth decay and provides excellent mouth feel and after taste. Further the compositions of the present invention protect the mouth from bad breath and gum disease, thereby promoting complete oral hygiene. The compositions of the present invention are stable and devoid of any incompatibilities between the excipients used. The compositions of the present invention are stable over the entire shelf life.

In one embodiment, the effervescent dosage forms of the present invention are packed with dessicants, such as, but not limited to, anhydrous silica gel, anhydrous sodium sulfate, anhydrous sodium, calcium or magnesium carbonate, and the like to maintain the anhydrous condition of the dosage form. The compositions of the present invention can be presented in the form of stick pack, sachets, pouches, standard blister packs, Alu-Alu blister packs, strip packs, bottles and the like in unit dose or multiple dose presentations.

The oral care compositions of the present invention are prepared by methods such as, but not limited to, physical admixture, wet granulation, dry granulation, direct compression. In one embodiment, when the carbon dioxide source used in the composition of the present invention is sodium bicarbonate, the process employed to prepare the compositions of the present invention comprises the step of "curing" sodium bicarbonate by heating it to, e.g., 90° C. which stabilizes the system by virtue of the formation of surface sodium carbonate, which acts as a moisture scavenger. In one embodiment, the compositions of the present invention are prepared by the process of wet granulation using a binder solution.

In one embodiment is provided method of using the compositions of the present invention for cleaning oral cavity and maintaining oral hygiene comprising the steps of: (a) placing into an oral cavity the composition of the present invention comprising at least one carbon dioxide source, at least one acid source, at least one abrasive and one or more pharmaceutically acceptable excipients; (b) dispersing or solubilizing said oral composition; (c) using the resulting saliva mixture to remove organic debris and biomass from the teeth; and (d) expelling or swallowing the resulting saliva mixture. In another embodiment is provided use of oral care compositions of the present invention for preventing dental caries and plaque formation and treating halitosis or gum diseases. In a further embodiment is provided use of oral care compositions of the present invention for maintenance of oral hygiene. In a further embodiment, the present invention provides a method of maintaining oral health comprising administering to a human or animal subject in need thereof compositions of the present invention.

While the present invention has been described in terms of its exemplary embodiments, certain modifications and equivalents will be apparent to those skilled, in the art and are intended to be included within the scope of the present invention. The invention is, further illustrated by the following examples, which are for illustrative purposes and should not be construed as limiting the scope of the invention in any way.

EXAMPLES

Example 1

Oral Rinse Powder

TABLE 1

Composition of oral rinse powder

| Ingredients | mg/unit |
|---|---|
| Sodium bicarbonate, USP | 1250 |
| Citric acid anhydrous, USP/NF | 250 |
| Co-processed excipient of calcium silicate and mannitol (PanExcea™ MC 200G) | 600 |
| Xylitol, USP/NF | 200 |
| Sodium lauryl sulfate, Ph. Eur | 22 |
| Mint flavoring agent | 3 |
| Menthol, USP | 25 |
| Aspartame, USP | 150 |
| Total | 2500 |

Procedure: The above ingredients were blended for 30 minutes under conditions of low shear, to produce oral rinse powder.

Example 2

Oral Rinse Powder

TABLE 2

Composition of oral rinse powder

| Ingredients | mg/unit |
|---|---|
| Sodium bicarbonate, USP | 1250 |
| Citric acid anhydrous, USP/NF | 250 |
| Co-processed excipient of calcium silicate and mannitol (PanExcea™ MC 200G) | 600 |
| Xylitol, USP/NF | 200 |
| Sodium lauryl sulfate, Ph. Eur. | 22 |
| Mint flavoring agent | 3 |
| Menthol, USP | 22 |
| *Eucalyptus* oil | 3 |
| Acesulfame potassium, Ph. Eur. | 150 |
| Total | 2500 |

Procedure: Eucalyptus oil was adsorbed on a blend of xylitol and co-processed excipient of calcium silicate and mannitol. To the above blend were added the remaining excipients and the mixture was blended for 30 minutes under conditions of low shear, to produce oral rinse powder.

Example 3

Fast Dissolving Oral Rinse Tablets

TABLE 3

Composition of fast dissolving oral rinse tablets

| Ingredients | mg/unit |
|---|---|
| Sodium bicarbonate, USP | 1150 |
| Citric acid anhydrous, USP/NF | 150 |
| Co-processed excipient of calcium silicate and mannitol (PanExcea™ MC 200G) | 600 |
| Xylitol, USP/NF | 200 |
| PEG-40 sorbitan diisostearate | 20 |
| Hydroxypropyl methyl cellulose, USP | 55 |
| Maize starch, USP | 125 |
| Menthol, USP | 25 |
| Aspartame, USP | 150 |
| Cetyl pyridinium chloride, USP/NF | 1 |
| Mint flavoring agent | 4 |
| Magnesium stearate, USP | 20 |
| Total | 2500 |

Procedure: Sodium bicarbonate, maize starch, sodium lauryl sulfate were admixed, and granulated with solution of hydroxypropyl methyl cellulose in isopropyl alcohol, dried and sized. The remaining ingredients were blended separately and admixed with the sized granule. The blend was lubricated and compressed into oral rinse tablets.

Example 4

Fast Dissolving Oral Rinse Granules

TABLE 4

Composition of fast dissolving oral rinse granules

| Ingredients | mg/unit |
|---|---|
| Sodium bicarbonate, USP | 1150 |
| Citric acid anhydrous, USP/NF | 150 |
| Co-processed excipient of calcium silicate and mannitol (PanExcea™ MC 200G) | 700 |
| Xylitol, USP/NF | 275 |
| Microcrystalline cellulose, USP | 180 |
| Sodium lauryl sulfate, Ph. Eur. | 20 |
| Bubble gum flavoring | 3.5 |
| Hydroxypropyl methyl cellulose, USP | 65 |
| Thymol, USP/NF | 14 |
| Menthol, USP | 22 |
| Aspartame, USP | 150 |
| Stannous fluoride, USP | 0.5 |
| Magnesium stearate, USP | 20 |
| Total | 2750 |

Procedure: All the ingredients were admixed, and granulated with solution of hydroxypropyl methyl cellulose in isopropyl alcohol, dried and sized to give oral rinse granules.

We claim:

1. An oral care composition comprising at least one carbon dioxide source, wherein the at least one carbon dioxide source is sodium bicarbonate,
    at least one acid source, wherein the at least one acid source is citric acid,
    at least one co-processed abrasive, wherein the at least one co-processed abrasive is a co-processed excipient comprising calcium silicate and mannitol, and
    one or more pharmaceutically acceptable excipients.

2. The oral care composition of claim 1, wherein the pharmaceutically acceptable excipient is a sweetening agent, flavouring agent, surfactant, viscosity modifier, binder, disintegrant, glidant, anti-adherent, lubricant, diluent, humectant, chelating or sequestering agent, pH modifier, buffering agent, opacifier, colorant or pigment, adhesive, liquid carrier or a mixture thereof.

3. The oral care composition of claim 1, wherein the composition further comprises an oral care agent.

4. The oral care composition of claim 3, wherein the oral care agent is an anti-bacterial, antimicrobial, anti-plaque agent, astringent agent, desensitizing agent, fluoride containing anticaries agent, hydrogen peroxide source, tartar control agent, anticalculus agent, fluoride ion source, stannous ion source, anesthetic agent, whitening agent, tooth strengthening agent, anti-malodor agent, anti-gingivitis agent, anti-periodontitis agent, anti-sensitivity agent, anti-erosion agent, anti-xerostomia agent, occlusion agent, antiseptic agent, antioxidant, proteolytic enzyme, antistain agent, healing agent, nutrient, probiotic, remineralization agent, anti-inflammatory agent, analgesic agent, antibiotic, vitamin, antiviral agent, antifungal agent or a combination thereof.

5. The oral care composition of claim 4, wherein the oral care agent is an anti-bacterial, antimicrobial, anti-plaque agent, desensitizing agent, fluoride ion source, anesthetic agent, whitening agent, anti-malodor agent, anti-gingivitis agent, remineralization agent, or a combination thereof.

6. The oral care composition of claim 1, wherein the composition is in the form of fast dissolving powder, quick dissolving granules, fast dissolving tablets, bite dispersion tablets, capsules, lozenge, films, non-aqueous liquid mixtures, oral rinse, mouth wash, toothpaste, tooth powder, oral tablet, denture product, or chewing gum.

7. An oral care composition comprising
 (i) sodium bicarbonate,
 (ii) citric acid,
 (iii) a co-processed abrasive consisting essentially of calcium silicate and mannitol, and
 (iv) one or more pharmaceutically acceptable excipients.

8. The oral care composition of claim 1, wherein the composition comprises about 5 to about 90% by weight of the at least one carbon dioxide source, about 1 to about 50% by weight of the at least one acid source, and about 1 to about 95% by weight of the at least one co-processed abrasive.

9. The oral care composition of claim 7, wherein the composition comprises about 5 to about 90% by weight of sodium bicarbonate, about 1 to about 50% by weight of citric acid, and about 1 to about 95% by weight of the co-processed abrasive.

* * * * *